United States Patent [19]
Luderer et al.

[11] Patent Number: 5,698,402
[45] Date of Patent: Dec. 16, 1997

[54] METHODS FOR DIAGNOSING BENIGN PROSTATIC HYPERPLASIA

[75] Inventors: Albert A. Luderer, Weston; Grant D. Carlson, Orange; Robert P. Thiel, Bethany; Thomas F. Soriano, Ansonia; William J. Kramp, Woodbridge, all of Conn.

[73] Assignee: Dianon Systems, Inc., Stratford, Conn.

[21] Appl. No.: 393,214

[22] Filed: Feb. 23, 1995

[51] Int. Cl.[6] .................... G01N 33/573; G01N 33/574; G01N 33/68

[52] U.S. Cl. .................... 435/7.4; 128/898; 435/7.94; 436/64; 436/86

[58] Field of Search .................... 128/630, 898; 435/7.4, 7.94; 436/64, 86

[56] References Cited

U.S. PATENT DOCUMENTS 5,501,983  3/1996  Lilja et al. .................... 436/518

OTHER PUBLICATIONS

Oesterling et al. Influence of Patient Age on the Serum PSA Concentration. Urologic Clinics of North America. vol. 20, No. 4, pp. 671–680, Nov. 1993.

A. Christensson et al. Serum Prostate Specific Antigen Complexed to 1-Antichymotrypsin as an Indicator of Prostate Cancer, The Journal of Urology, vol. 150 pp. 100–105, Jul. 1993.

Primary Examiner—Jennifer Bahr
Assistant Examiner—Samuel Gilbert
Attorney, Agent, or Firm—Brian D. Voyce

[57] ABSTRACT

The present invention relates to a method for diagnosing benign prostatic hyperplasia (BPH) in a male human patient without requiring a biopsy. The total prostate specific antigen (PSA) level in the blood or serum of the patient is measured. If the patient has a total PSA level of between 2.5 ng/ml, (4.0 ng/ml for those 60 years or over), and 10.0 ng/ml, then the free PSA level in the blood or serum of the patient is measured. The proportion of free PSA to total PSA is calculated. If this proportion is equal to or greater than about 25%, then the patient is diagnosed as having BPH.

2 Claims, 5 Drawing Sheets

FIGURE 4

| DIAGNOSTIC REPORT | | PATIENT: _____ |
|---|---|---|
| TOTAL PSA | F/T RATIO | DIAGNOSIS |
| 5.0 ng/ml | >45% | BPH |

METHODS FOR DIAGNOSING BENIGN PROSTATIC HYPERPLASIA

TECHNICAL FIELD

The present invention relates to a method for diagnosing benign prostatic hyperplasia (BPH) in a male human patient without requiring a biopsy. The total prostate specific antigen (PSA) level in the blood or serum of the patient is measured. If the patient has a total PSA level of between 2.5 ng/ml, (4.0 ng/ml for those 60 years or over), and 10.0 ng/ml, then the free PSA level in the blood or serum of the patient is measured. The proportion of free PSA to total PSA is calculated. If this proportion is equal to or greater than about 25%, then the patient is diagnosed as having BPH.

BACKGROUND ART

Prostate specific antigen (PSA) is recognized as a molecular marker for prostatic adenocarcinoma (CAP). Blood or serum based immunoassays measuring the total PSA level have been commercially available for a number of years. However, the detection of total PSA does not necessarily mean that a patient has CAP. In order to distinguish CAP, a total PSA test has to satisfy two elements: a high sensitivity—the ability to detect disease when present, and a high specificity—the ability to detect true negatives and avoid false positives. From clinical experience, total PSA tests have become accepted as being predictive of CAP if the total PSA level is greater than 10.0 ng/ml. Total PSA values between 0.0 ng/ml and about 3.9 ng/ml have been predictive of no disease being present, with a value of about 2.5 ng/ml being used for men under 60 years old.

PSA is primarily organ-specific, not cancer specific. Thus, PSA in blood or serum can result not only from CAP, but also from normal or hyperplastic prostate tissues. Below 10.0 ng/ml, a total PSA test cannot distinguish BPH from CAP. Studies have found that 43% (136/319) of patients with organ-confined CAP have a total PSA value within the normal range of less than 4.0 ng/ml. Moreover, about 25% (148/597) of men with BPH have a total PSA value above 4.0 ng/ml. (See Oesterling, J. E., "Prostate Specific Antigen: A Critical Assessment of the Most Useful Tumor Marker for Adenocarcinoma of the Prostate", *J. Urol.*, Vol:145, 907–923, 1991.) Standard medical practice is to biopsy patients having total PSA levels of between 4.0 ng/ml and 10.0 ng/ml because about 30% of those patients have CAP.

One proposed method for detecting CAP is disclosed in SER. NO. WO 92/01936 to Hans Lilja et al., (Lilja application), filed Jul. 22, 1991, under the Patent Cooperation Treaty (PCT). In general, the Lilja application discloses using immunoassays to measure free PSA and a complexed form of PSA. Free PSA is a 33 kDa single chain glycoenzyme that is produced by the epithelial cells lining the acini and prostatic ducts of the prostate gland. Complexed PSA refers primarily to a 90 kDa complex of PSA bound to alpha 1—antichymotrypsin (ACT) protein. Free PSA and complexed PSA, and their proportions are applied in the diagnosis of patients with CAP. Throughout, the specification discloses using a combination of a free PSA to total PSA (F/T) proportion and a complexed PSA to total PSA (C/T) proportion for use in diagnosing CAP. No prostate needle biopsy were performed on the patients, and the patients covered a full range of total PSA values. The text provides no guidance as to specifically how one uses these proportions.

SUMMARY OF THE INVENTION

The present invention relates to a method for diagnosing BPH in a male human patient without requiring a biopsy. Presently, if a patient has a total PSA level of 4.0 ng/ml to 10.0 ng/ml, then he must undergo a prostate needle biopsy, an anesthetic-free operation performed transrectally involving substantial pain and discomfort, especially if a sextant biopsy is performed which requires taking six samples. The present method eliminates the need for about one-third of those patients to undergo such a biopsy.

The method comprises four steps. First, if the patient is under 60 years old, one measures the PSA level in the blood or serum of the patient. Second, one measures the free PSA level in the blood or serum of a patient, but only if he has a total PSA level of between 2.5 ng/ml and 10.0 ng/ml, if under 60 years of age. If the patient has a total PSA level below 2.5 ng/ml, then he is diagnosed to have BPH. If the patient has a total PSA level above 10.0 ng/ml, then he is diagnosed to have CAP. Third, one calculates the proportion of free PSA to total PSA. Fourth and finally, one diagnoses the patient as having BPH if the calculated proportion of free PSA to total PSA is equal to or greater than about 25%. If the patient is at least 60 years old, then one performs the same steps, but the cutoff level for total PSA before proceeding with the second step is 4.0 ng/ml.

A report for a diagnosis of BPH in a male human patient without requiring a biopsy comprises listing a total PSA level of between 2.5 ng/ml, (4.0 ng/ml for those at least 60 years old), and 10.0 ng/ml and listing a free PSA to total PSA proportion equal to or greater than about 25%.

BRIEF DESCRIPTION OF THE DRAWINGS

FIG. 4 a view of a pathology report according to the present invention.

PREFERRED EMBODIMENTS

Assays

Figure 1:
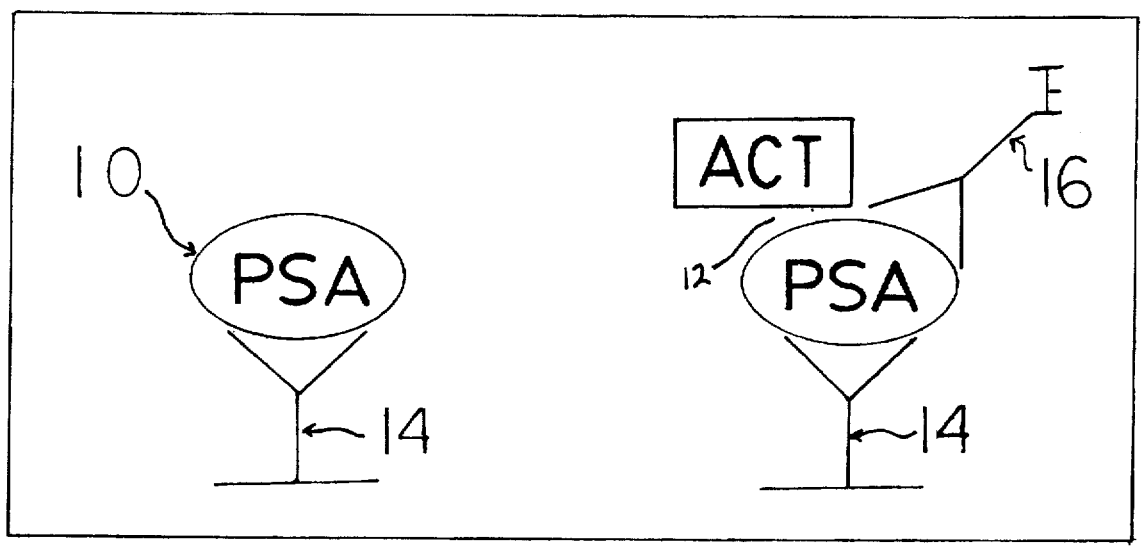
FIG. 1 is a diagrammatic view of the total PSA assay used in the present invention.

In a preferred embodiment, the present method comprises two immunoassays. The first assay is a total PSA sandwich immunoassay manufactured by Tosoh Medics, Inc. (Tosoh) of Foster City, Calif. The assay is an immunoenzymetric assay using dual murine monoclonal antibodies. FIG. 1 shows diagrammatically how, in the final sandwich configurations, this first assay captures both free PSA (10) and complexed PSA/ACT (12) using a capture antibody (14) and an enzyme labelled antibody (16).

Figure 2:
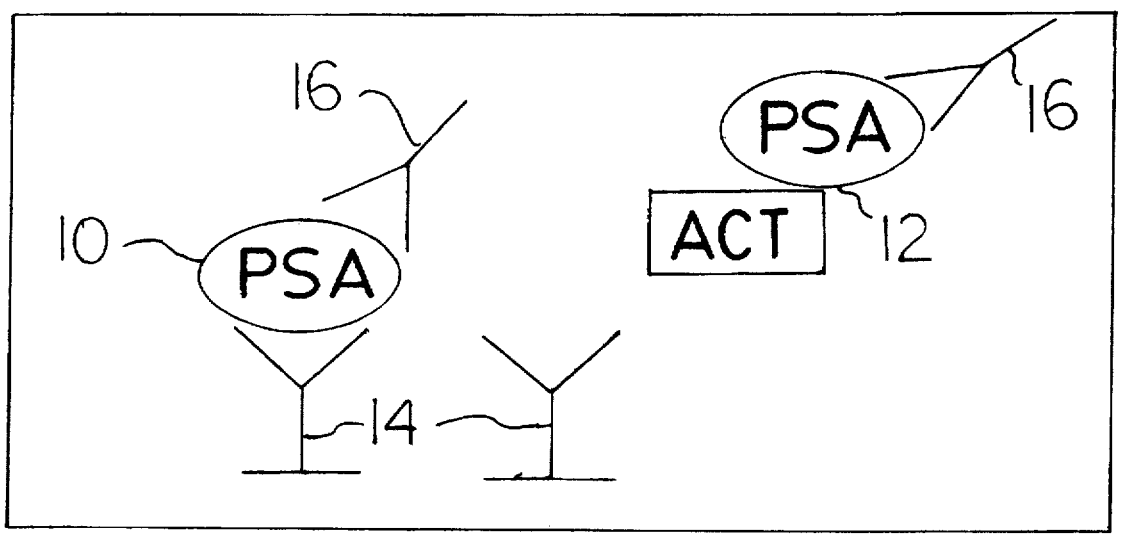
FIG. 2 is a diagrammatic view of the free PSA assay used in the present invention.

The second assay is a free PSA immunoassay manufactured developed by Immuno Corp. for Dianon Systems, Inc. (Dianon) of Stratford, Conn. This free PSA test is designed to detect free PSA in serum using an IRMA coated tube format. Free PSA binds to a tube coated by a monoclonal antibody which selectively binds free PSA but not complexed PSA. After washing, an $I^{125}$ labelled polyclonal antibody against free PSA is reacted with the bound free PSA. The physician is given a result that expresses a proportion of free PSA to total PSA. FIG. 2 show diagrammatically how in the final sandwich configuration, this second assay captures free PSA (10), but the capture antibody does not specifically bind to the complex of the PSA/ACT complex (12) and radiolabelled antibody (16).

EXAMPLE

In a clinical study to validate the present invention, 216 patients were tested. Classified as "normals", 96 males were identified as being between 45 years and 75 years old and having a normal PSA (i.e., less than 2.5 ng/ml total PSA if under 60 years old and less than 4.0 if over 60 years old), a normal digital rectal examination (DRE), and no history of CAP. The age mean was 57. Classified as "BPH", 65 males were identified as being between 45 years old and 75 years old, having BPH histologically confirmed by sextant needle prostate biopsy, and no history of cancer. The age mean was 61. Classified as "CAP", 55 males were identified as being between 45 years old and 75 years old and having primary CAP histologically confirmed by needle prostate biopsy. The age mean was 64. None of the above patients received any form of prostate-related treatment prior to blood draw. Total PSA was measured using the Tosoh assay described above, in accordance with the manufacturer's instructions. Free PSA was measured using the Dianon assay described above, in accordance with the manufacturer's instructions.

If one restricts the patient population to those 25 CAP patients and 34 BPH patients having a total PSA range of between 4.0 ng/ml to 10.0 ng/ml, the use of a total PSA blood or serum test alone does not provide any ability to distinguish between cancer patient or BPH patients.

TABLE 1

|  | BPH | CAP |
| --- | --- | --- |
| Mean | 6.13 | 6.92 |
| Median | 5.80 | 6.90 |
| 95% Confidence level for Mean | 5.62–6.64 | 6.20–7.65 |

There is no statistically relevant difference in these results.

While the addition of the step of measuring free PSA and the calculation of a free PSA to total PSA proportion did produce a marked delineation between the mean values for CAP patients and the others, in the suspect group having a total PSA level of between 2.5 ng/ml, (4.0 ng/ml for those 60 years old or over), and 10.0 ng/ml there was no use for the mean values alone as a diagnostic modality.

TABLE 2

|  | BPH | CAP |
| --- | --- | --- |
| Mean (%) | 21 | 13 |
| Median (%) | 19 | 14 |
| 95% Confidence level for Mean (%) | 18–24 | 11–16 |

However, if the patients are restricted to those having a total PSA of from 2.5 ng/ml, (4.0 ng/ml for those 60 or over), to 10.0 ng/ml, and sensitivity/specificity relationships are examined with respect to F/T proportions, then significantly different results are obtained. One can differentiate certain BPH patients with great certainty using a F/T proportion cutoff of greater than about 25%. The following table shows the relationship between F/T proportion and sensitivity/specificity:

TABLE 3

| F/T PSA Proportion | Sensitivity | Specificity |
| --- | --- | --- |
| <7% | 20% | 97% |
| <10% | 24% | 85% |
| <12% | 36% | 79% |

TABLE 3-continued

| F/T PSA Proportion | Sensitivity | Specificity |
| --- | --- | --- |
| <15% | 72% | 73% |
| <18% | 84% | 50% |
| <20% | 88% | 47% |
| <25% | 100% | 30% |
| <30% | 100% | 15% |

(Here, sensitivity is reported with respect to CAP, thus at an F/T proportion of <25%, the 100% figure means that all CAP patients are present. Conversely, at an F/T proportion of >25% no CAP patients, only BPH patients are present.) By using the about 25% F/T proportion level as a cutoff point for patients having a total PSA of between 2.5 ng/ml, (4.0 ng/ml for those at least 60 years old), and 10.0 ng/ml, one can diagnose a patient pool that is 100% composed of patients having BPH. These patients can forego an invasive and painful transrectal needle biopsy.

Figure 3:
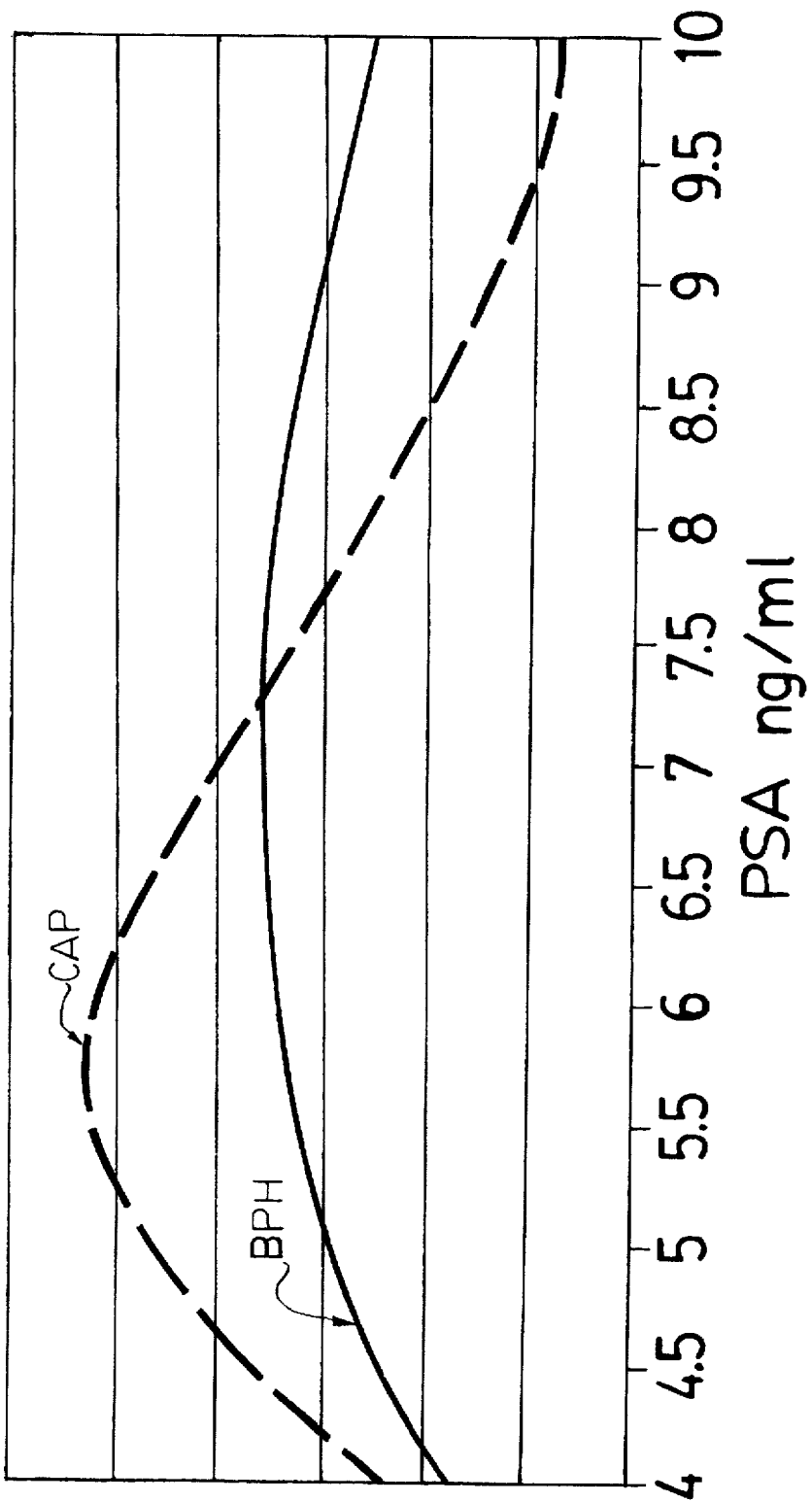
FIG. 3 a graph showing the distribution of total PSA levels for BPH patients and CAP patients in the Example.
Figure 5:
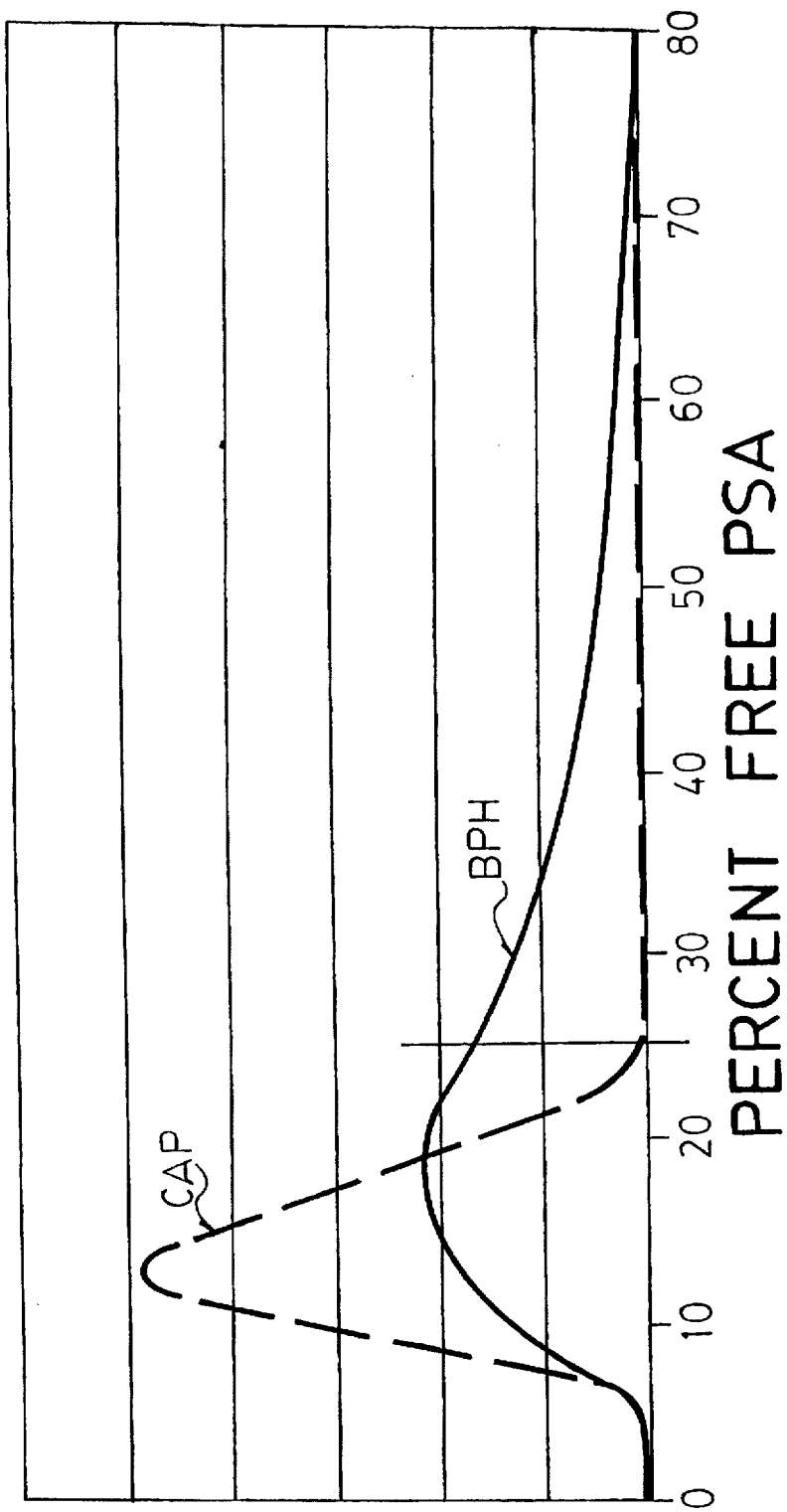
FIG. 5 is a graph showing the distribution of F/T proportions for BPH patients and CAP patients in the Example.

Graphic evidence of the discriminating power of the present method can be found in FIGS. 3 and 5. FIG. 3 show the distribution of the total PSA blood or serum levels in patients within the select total PSA range of either 2.5 ng/ml or 4.0 ng/ml, depending upon age, and 10.0 ng/ml. One can easily see the lack of a separation between the CAP patients and the BPH patients. FIG. 5 shows the distribution of the F/T proportion in those same patients. Clearly the CAP patients can be separated from certain BPH patients by using the about 25% mark.

Using the present method, and in view of the above clinical data, one can expect the following scenario if 1000 patients are screened, each having the requisite minimum total PSA. A total of 250 patients will have CAP. Of those, 100% will have a F/T proportion less than about 25%. The bulk of the 1000 patients (750) will have BPH. Of those, 70%, or 525 patients, will have a F/T proportion less than about 25%. The remaining 30% of the BPH patients will have a F/T proportion greater than about 25%. By using the present method to diagnose BPH, none of the patients having CAP and a total PSA of between 2.5 ng/ml, (4.0 ng/ml for those at least 60 years old), and 10.0 ng/ml will escape detection. Moreover, about one-third of the BPH patients would be prevented from having to undergo a painful transrectal biopsy.

In a time of increasing concern about health care costs and unnecessary medical procedures, the present method provides a powerful cost-saving clinical tool to the urologist. Only patients having a total PSA level of from 2.5 ng/ml, (4.0 ng/ml for those at least 60 years old), and 10.0 ng/ml need to have a second blood or serum test performed. Using the present method, 30% of the patients do not need biopsies. Moreover, about one-third of the patients biopsied will have CAP, a substantial enrichment from current practice.

FIG. 4 illustrates a pathology report that uses the present method. The report includes a listing of the results of a first assay for total PSA. The total PSA level for the patient is between 2.5 ng/ml, (4.0 ng/ml for those at least 60 years old), and 10 ng/ml. It also includes a listing of a calculation occurring from a free PSA assay —the free PSA to total PSA proportion. The F/T proportion is equal to or greater than about 25%. Finally, the report includes a diagnosis of the patient having BPH.

All publications or unpublished patent applications mentioned herein are hereby incorporated by reference thereto.

Other embodiments of the present invention are not presented here which are obvious to those of skill in the art, now or during the term of any patent issuing herefrom, and thus, are within the spirit and scope of the present invention.

We claim:

1. A method for diagnosing benign prostatic hyperplasia (BPH) in a male human patient under 60 years old without requiring a prostate biopsy comprising:
   a) measuring the total prostate specific antigen (PSA) level in the blood or serum of the patient;
   b) measuring the free PSA level in the blood or serum of a patient only if said patient has a total PSA level of between 2.5 ng/ml and 10.0 ng/ml;
   c) calculating the proportion of free PSA to total PSA; and
   d) diagnosing the patient as having BPH if the calculated proportion of free PSA to total PSA is equal to or greater than about 25%.

2. A method for diagnosing benign prostatic hyperplasia (BPH) in a male human patient at least 60 years old without requiring a prostate biopsy comprising:
   a) measuring the total prostate specific antigen (PSA) level in the blood or serum of the patient;
   b) measuring the free PSA level in the blood or serum of a patient only if said patient has a total PSA level of between 4.0 ng/ml and 10.0 ng/ml;
   c) calculating the proportion of free PSA to total PSA; and
   d) diagnosing the patient as having BPH if the calculated proportion of free PSA to total PSA is equal to or greater than about 25%.

* * * * *